(12) United States Patent
Treado et al.

(10) Patent No.: US 11,935,650 B2
(45) Date of Patent: Mar. 19, 2024

(54) METHOD FOR FUSING SENSOR DATA FOR CARDIAC MONITORING AND DEVICES THEREOF

(71) Applicant: CHEMIMAGE CORPORATION, Pittsburgh, PA (US)

(72) Inventors: Patrick J. Treado, Pittsburgh, PA (US); Aaron G. Smith, Monroeville, PA (US); Heather E. Gomer, Sewickley, PA (US); Lewis L Lanker, Pittsburgh, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 135 days.

(21) Appl. No.: 17/335,857

(22) Filed: Jun. 1, 2021

(65) Prior Publication Data

US 2021/0369208 A1 Dec. 2, 2021

Related U.S. Application Data

(60) Provisional application No. 63/032,894, filed on Jun. 1, 2020.

(51) Int. Cl.
| | |
|---|---|
| *G16H 40/67* | (2018.01) |
| *A61B 5/00* | (2006.01) |
| *A61B 5/0205* | (2006.01) |
| *A61B 5/318* | (2021.01) |
| *G06F 18/25* | (2023.01) |
| *G06V 10/80* | (2022.01) |
| *G06V 20/52* | (2022.01) |

(Continued)

(52) U.S. Cl.
CPC ........... *G16H 40/67* (2018.01); *A61B 5/0205* (2013.01); *A61B 5/318* (2021.01); *A61B 5/4878* (2013.01); *A61B 5/7267* (2013.01); *A61B 5/7275* (2013.01); *A61B 5/7282* (2013.01); *G06F 18/251* (2023.01); *G06V 10/80* (2022.01); *G06V 20/52* (2022.01); *G16H 30/40* (2018.01); *G16H 50/30* (2018.01); *A61B 5/14551* (2013.01)

(58) Field of Classification Search
CPC ........ G16H 40/67; G16H 50/30; G16H 30/40; G06V 20/52; G06V 10/80; A61B 5/0205; A61B 5/4878; A61B 5/7267; A61B 5/7275; A61B 5/7282; A61B 5/318; A61B 5/14551
USPC ......................................... 600/301
See application file for complete search history.

(56) References Cited

U.S. PATENT DOCUMENTS 6,332,091 B1 * 12/2001 Burns .................. A61B 5/0059
600/475
8,694,089 B2 * 4/2014 Arad (Abboud) ... A61B 5/0044
600/509

(Continued)

*Primary Examiner* — Carl H Layno
*Assistant Examiner* — Michael J Lau
(74) *Attorney, Agent, or Firm* — DLA Piper LLP (US)

(57) ABSTRACT

A method for improved cardiac monitoring is disclosed. The method includes receiving image data from an image sensor configured for monitoring edema in a patient. Additional data is received from one or more additional sensors configured to monitor one or more factors related to cardiac activity of the patient. The received image data is fused with the received additional data from the one or more additional sensors to generate fused data set. A cardiac condition for the patient is determined based on the fused data set. A cardiac monitoring computing device and non-transitory medium are also disclosed.

21 Claims, 3 Drawing Sheets

(51) Int. Cl.
  *G16H 30/40* (2018.01)
  *G16H 50/30* (2018.01)
  *A61B 5/1455* (2006.01)

(56) References Cited

U.S. PATENT DOCUMENTS

| | | |
|---|---|---|
| 2007/0127789 A1 | 6/2007 | Hoppel et al. |
| 2012/0157856 A1 | 6/2012 | An et al. |
| 2013/0159350 A1 | 6/2013 | Sankar et al. |
| 2014/0276166 A1* | 9/2014 | Drori .................. A61B 5/0537 |
| | | 702/19 |
| 2015/0250428 A1* | 9/2015 | Zhang .................... G16Z 99/00 |
| | | 600/300 |
| 2016/0000338 A1 | 1/2016 | Zhang et al. |
| 2017/0079530 A1* | 3/2017 | DiMaio ................ A61B 5/0261 |
| 2017/0245759 A1* | 8/2017 | Jain ........................ A61B 5/163 |
| 2019/0231260 A1* | 8/2019 | Stewart ................ A61B 5/4869 |
| 2019/0298998 A1* | 10/2019 | Coleman ................ A61B 5/389 |
| 2019/0336076 A1* | 11/2019 | Kuhn .................... A61B 5/0261 |
| 2020/0022649 A1* | 1/2020 | Rodriguez ........... A61B 5/4878 |

\* cited by examiner

METHOD FOR FUSING SENSOR DATA FOR CARDIAC MONITORING AND DEVICES THEREOF

CROSS-REFERENCE TO RELATED APPLICATIONS

This application claims the benefit of U.S. Provisional Patent Application No. 63/032,894 filed Jun. 1, 2020, the entirety of which is incorporated by reference herein.

TECHNICAL FIELD

The present disclosure relates generally to systems and methods for improved cardiac monitoring. In particular, the present disclosure relates to systems and methods that improve cardiac monitoring by fusing sensor data. More particularly, the present disclosure relates to systems and methods that fuse image data related to peripheral edema with other non-image data to provide indications of potential heart failure.

BACKGROUND

Edema is a system of heart disease, including for example, congestive heart failure. Detection of the severity of peripheral edema is an important factor in determining treatment options to avoid light-threatening conditions, such as heart failure. For example, heart failure is the leading cause of hospitalization in people older than 65 and accounts for more hospital admissions that all forms of cancer combined. Of the patients admitted and treated for heart failure, nearly 25% of patients are readmitted within 30 days of discharge. Readmission is often necessary because diuretics prescribed for heart failure patients can require frequent adjustments. When dosing is missed or adjustments to drug levels are not monitored, buildup of edema is one of the first indicators that modifications may need to be made to a patient's treatment regimen. Thus, monitoring edema is an important aspect of monitoring a patient for potential heart failure.

Currently, clinicians have various techniques for monitoring a patient after discharge. For example, a clinician can schedule regular follow-up appointments, track a patient's exercise tolerance and symptoms, monitor a patient's electrolyte levels, monitor a patient for medicinal side effects, and prescribe a tele-monitoring regiment to the patient, including, for example, monitoring blood pressure, heart rate, body weight, and other related patient health parameters.

However, recent studies have shown that current tele-monitoring techniques related to monitoring of, for example, weight and various vital signs in heart failure patients as an adjunct to routine care has no significant incremental impact on morbidity and mortality. Systems have been developed to utilize imaging data to detect peripheral edema in order to improve tele-monitoring of patient's for potential heart failure. However, there is a need for systems that can more accurately provide early and objective advance warning of potential heart failure.

The present disclosure is directed to this and other advantageous improvements cardiac monitoring.

SUMMARY

In one embodiment, there is a method of cardiac monitoring, the method comprising: receiving, by a cardiac monitoring computing device, image data from an image sensor configured for monitoring edema in a patient; receiving, by the cardiac monitoring computing device, additional data from one or more additional sensors configured to monitor one or more factors related to cardiac activity of the patient; fusing, by the cardiac monitoring computing device, the received image data with the received additional data from the one or more additional sensors to generate a fused data set; and determining, by the cardiac monitoring computing device, a cardiac condition for the patient based on the fused data set.

In another embodiment, fusing the received image date with the received additional data further comprises: applying, by the cardiac monitoring computing device, one or more data fusion algorithms to the received image data and the received additional data.

In another embodiment, applying the data fusion algorithm comprises utilizing one or more of an image weighted Bayesian function, logistic regression, linear regression, regression with regularization, naïve Bayes, classification and regression tress, support vector machines, or a neural network.

In another embodiment, the received additional data is non-image data.

In another embodiment, the one or more additional sensors comprise one or more of a pulse oximeter, an electrocardiogram machine, a sensor for thoracic impedance, or an implantable cardiac monitoring device.

In another embodiment, determining the cardiac condition further comprises: identifying, by the cardiac monitoring computing device, one or more indications of a potential heart failure.

In another embodiment, the image sensor comprises: a light source configured to irradiate a tissue of the patient with light; and a detector configured to collect reflected light from the tissue of the patient and generate the image data associated with the reflected light; wherein the method further comprises: receiving, by the cardiac monitoring computing device, the image data associated with the reflected light; calculating, by the cardiac monitoring computing device, intensity values for reflected light; and determining, by the cardiac monitoring computing device, whether the tissue exhibits symptoms of edema.

In another embodiment, the tissue of the patient is located on a forearm of the patient.

In another embodiment, the image data is spectral data and the image sensor is a spectral sensor.

In one embodiment, there is a non-transitory computer readable medium having stored thereon instructions for improved cardiac monitoring comprising executable code that, when executed by one or more processors, causes the one or more processors to: receive image data from an image sensor configured for monitoring edema in a patient; receive additional data from one or more additional sensors configured to monitor one or more factors related to cardiac activity of the patient; fuse the received image data with the received additional data from the one or more additional sensors to generate a fused data set; and determine a cardiac condition for the patient based on the fused data set.

In another embodiment, the processors fuse the received image data with the received additional data by applying one or more data fusion algorithms to the received image data and the received additional data.

In another embodiment, the data fusion algorithm includes one or more of an image weighted Bayesian function, logistic regression, linear regression, regression with regularization, naïve Bayes, classification and regression tress, support vector machines, or a neural network.

In another embodiment, the additional data that the processors receive is non-image data.

In another embodiment, the one or more additional sensors comprise one or more of a pulse oximeter, an electrocardiogram machine, a sensor for thoracic impedance, or an implantable cardiac monitoring device.

In another embodiment, determination of the cardiac condition further comprises: identifying one or more indications of a potential heart failure.

In one embodiment, there is a cardiac monitoring computing device comprising memory comprising programmed instructions stored thereon for cardiac monitoring and one or more processors coupled to the memory and configured to execute the stored programmed instructions, which when the programmed instructions are executed the cardiac monitoring computing device: receives image data from an image sensor configured for monitoring edema in a patient; receives additional data from one or more additional sensors configured to monitor one or more factors related to cardiac activity of the patient; fuses the received image data with the received additional data from the one or more additional sensors to generate a fused data set; and determines a cardiac condition for the patient based on the fused data set.

In another embodiment, the processors fuse the received image data with the received additional data by applying one or more data fusion algorithms to the received image data and the received additional data.

In another embodiment, the data fusion algorithm includes one or more of an image weighted Bayesian function, logistic regression, linear regression, regression with regularization, naïve Bayes, classification and regression tress, support vector machines, or a neural network.

In another embodiment, the additional data that the processors receive is non-image data.

In another embodiment, the one or more additional sensors comprise one or more of a pulse oximeter, an electrocardiogram machine, a sensor for thoracic impedance, or an implantable cardiac monitoring device.

In another embodiment, determining the cardiac condition further comprises: identifying one or more indications of a potential heart failure.

In another embodiment, the image sensor comprises: a light source configured to irradiate a tissue of the patient with light; and a detector configured to collect reflected light from the tissue of the patient and generate the image data associated with the reflected light; wherein the cardiac monitoring computing device further: receives the image data associated with the reflected light; calculates intensity values for reflected light; and determines whether the tissue exhibits symptoms of edema.

In another embodiment, the image data is spectral data and the image sensor is a spectral sensor.

DRAWINGS

The accompanying drawings, which are incorporated in and form a part of the specification, illustrate the embodiments of the invention and together with the written description serve to explain the principles, characteristics, and features of the invention. In the drawings:

FIG. 1 a block diagram of a environment with an exemplary cardiac monitoring computing device;

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

Figure 1:
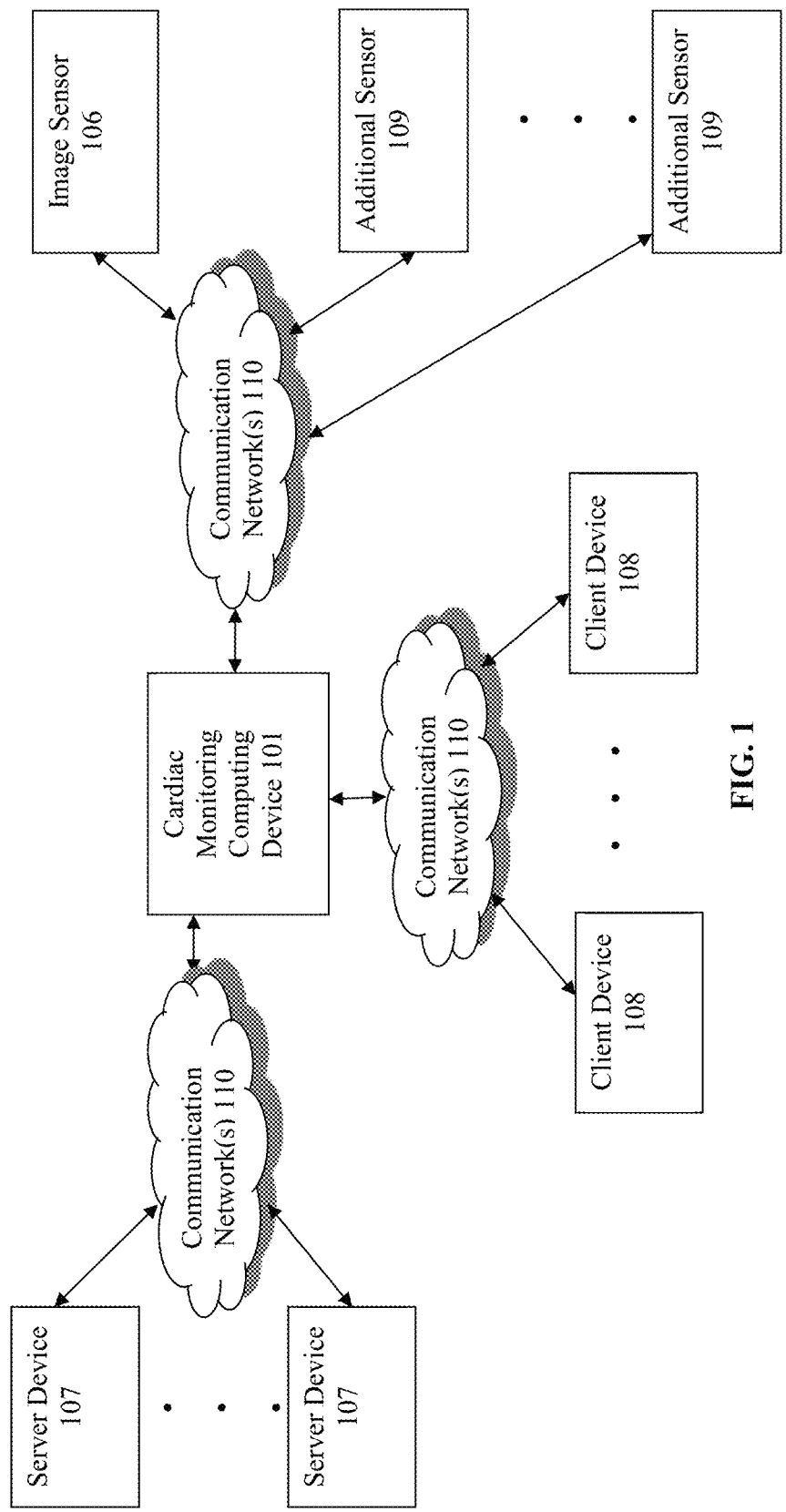

Referring to FIG. 1, an exemplary environment with an exemplary cardiac monitoring computing device is illustrated. The cardiac monitoring computing device in this example is coupled to a plurality of server devices 107, a plurality of client devices 108, an image sensor 106, and a plurality of additional sensors 109 via communication network(s) 110, although the cardiac monitoring computing device 101, server devices 107, image sensor 106, and/or additional sensors 109 may be coupled together via other topologies. This technology provides a number of advantages including providing methods, non-transitory computer readable media, and cardiac monitoring computing device 101s that provide improved cardiac monitoring. In particular, certain implementations of this technology utilize data fusion from multiple sensors, including image data related to peripheral edema, to provide more accurate and reliable, early, and objective indications of heart failure.

Figure 2:
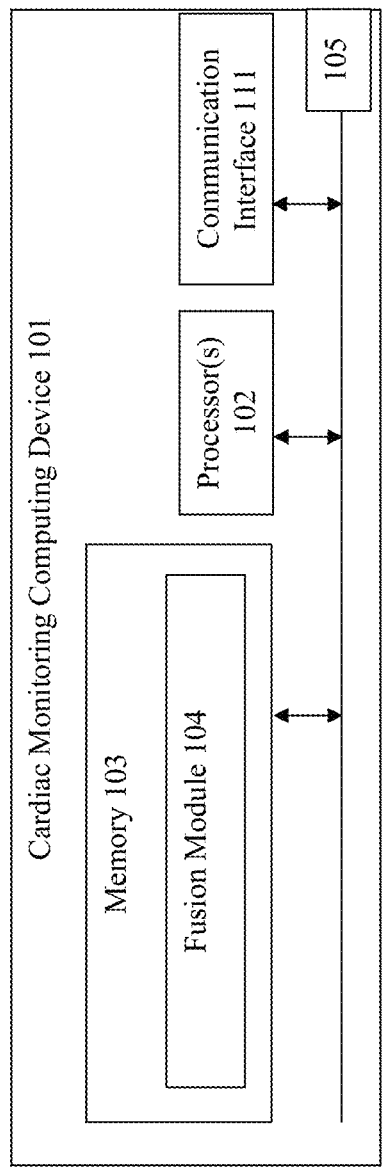
FIG. 2 is a block diagram of the exemplary cardiac monitoring computing device of FIG. 1.

Referring to FIGS. 1-2, the cardiac monitoring computing device 101 in this example includes processor(s) 102, a memory 103, and/or a communication interface 111, which are coupled together by a bus or other communication link 105, although the cardiac monitoring computing device 101 can include other types and/or numbers of elements in other configurations. The processor(s) 102 of the cardiac monitoring computing device 101 may execute programmed instructions stored in the memory 103 for the any number of the functions described and illustrated herein. The processor(s) 102 of the cardiac monitoring computing device 101 may include one or more CPUs or general purpose processors with one or more processing cores, for example, although other types of processor(s) can also be used.

The memory 103 of the cardiac monitoring computing device 101 stores these programmed instructions for one or more aspects of the present technology as described and illustrated herein, although some or all of the programmed instructions could be stored elsewhere. A variety of different types of memory storage devices, such as random access memory (RAM), read only memory (ROM), hard disk, solid state drives, flash memory, or other computer readable medium which is read from and written to by a magnetic, optical, or other reading and writing system that is coupled to the processor(s), can be used for the memory.

Figure 3:
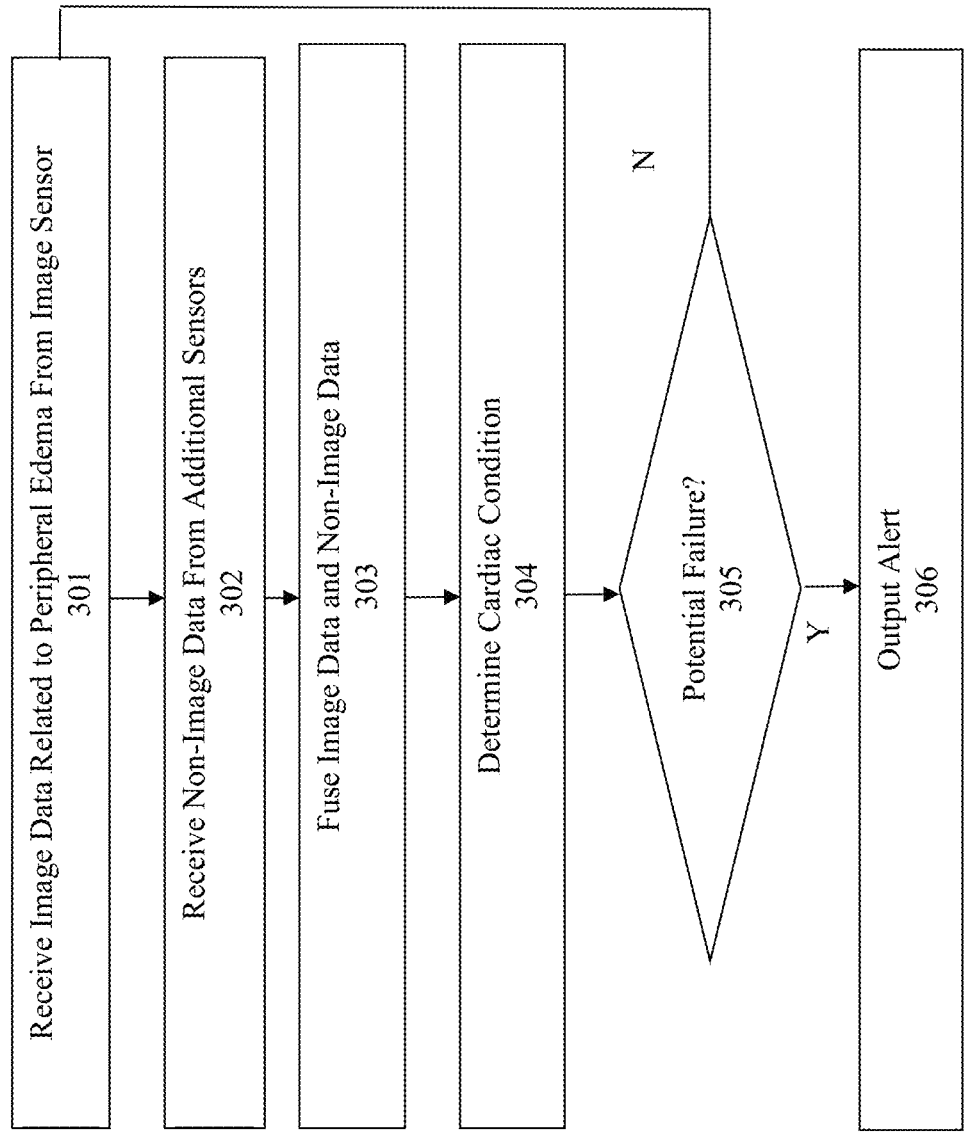
FIG. 3 is a flowchart of an exemplary method for improved, cardiac monitoring using sensor data fusion.

Accordingly, the memory of the cardiac monitoring computing device 101 can store application(s) that can include executable instructions that, when executed by the processor(s), cause the cardiac monitoring computing device 101 to perform actions, such as to perform the actions described and illustrated below with reference to FIG. 3. The application(s) can be implemented as modules or components of other application(s). Further, the application(s) can be implemented as operating system extensions, module, plugins, or the like.

Even further, the application(s) may be operative in a cloud-based computing environment. The application(s) can be executed within or as virtual machine(s) or virtual server(s) that may be managed in a cloud-based computing environment. Also, the application(s), and even the cardiac monitoring computing device itself, may be located in virtual server(s) running in a cloud-based computing environment rather than being tied to one or more specific physical network computing devices. Also, the application(s) may be running in one or more virtual machines (VMs) executing on the cardiac monitoring computing device 101. Additionally, in one or more embodiments of this technology, virtual machine(s) running on the cardiac monitoring computing device 101 may be managed or supervised by a hypervisor.

In this particular example, the memory 103 of the cardiac monitoring computing device 101 includes a fusion module 104, although the memory 103 can include other policies, modules, databases, or applications, for example. The fusion module 104 in this example is configured to fuse image data from the image sensor 106 with non-image data from one or more of the additional sensors, although the fusion module 104 could also fuse the image data with data received from one or more of the server devices 107. The fusion module 104 can fuse the image data from the image sensor 106 with data from any number and/or types of additional sensors 109. The fusion module 104 is configured to apply one or more data fusion algorithms to the image data from the image sensor 106 and the additional non-image data. By way of example only, the fusion module 104 may apply one or more of an image weighted Bayesian function, logistic regression, linear regression, regression with regularization, least angle regression, naïve Bayes, classification and regression tress (CART), support vector machines, relevance vector machines (RVM), neural network, or linear discriminant analysis to provide the fused data. The fusion module 104 advantageously fuses the image and non-image data to provide for cardiac monitoring as described in detail below with respect to the exemplary method illustrated in FIG. 3.

The communication interface 111 of the cardiac monitoring computing device operatively couples and communicates between the cardiac monitoring computing device, the image sensor, the additional sensors, the client devices and/or the server devices, which are all coupled together by the communication network(s) illustrated, although other types and/or numbers of communication networks or systems with other types and/or numbers of connections and/or configurations to other devices and/or elements can also be used.

By way of example only, the communication network(s) shown in FIG. 1 can include local area network(s) (LAN(s)) or wide area network(s) (WAN(s)), and can use TCP/IP over Ethernet and industry-standard protocols, although other types and/or numbers of protocols and/or communication networks can be used. The communication network(s) in this example can employ any suitable interface mechanisms and network communication technologies including, for example, teletraffic in any suitable form (e.g., voice, modem, and the like), Public Switched Telephone Network (PSTNs), Ethernet-based Packet Data Networks (PDNs), combinations thereof, and the like.

The cardiac monitoring computing device can be a standalone device or integrated with one or more other devices or apparatuses, such as the image sensor or the one or more of the server devices or the client devices, for example. In one particular example, the cardiac monitoring computing device can include or be hosted by one of the server devices or one of the client devices, and other arrangements are also possible.

In this example, the image sensor is a device configured for monitoring edema in the tissue of a patient. By way of example, the image sensor may be the system for detecting edema as disclosed in U.S. Patent Application Publication No. 2019-0231260, the disclosure of which is hereby incorporated by reference in its entirety. The image sensor allows for obtaining image data that can be utilized to measure peripheral edema for monitoring cardiac activity, including potential heart failure. The image sensor can advantageously be used to measure peripheral edema in non-shin locations, such as from the patient's forearm. Although the image sensor is illustrated as a standalone device, the image sensor could be incorporated in the cardiac monitoring computing device, or in one of the server devices or client devices.

In other embodiments, a spectral sensor is configured for monitoring edema in the tissue of a patient. The spectral sensor is not limited and includes sensors that determine the spectra that is emitted from tissue that of a patient that is suspected or is known to have edema. The edema is monitored by way of analysis of the spectra that is reflected from the tissue, and includes Raman spectroscopy or Fourier Transform Infrared Spectroscopy (FTIR), or any combination of these or similar techniques. In certain implementations of the spectral sensor, the spectral sensor generates spectral data, and the spectral data can be fused with additional data that is collected by additional sensors to thereby generate a fused data set.

The additional sensors are sensors know in the art that may be used to collect non-image data relevant to cardiac monitoring. By way of example only, the additional sensors can include a pulse oximeter (or other sensors configured to measure hemodynamics), an electrocardiogram (ECG or EKG), a sensor for measuring thoracic impedance, or an implantable cardiac monitoring device, although any other sensors capable of measuring data relevant to cardiac activity could be employed.

Each of the server devices in this example includes processor(s), a memory, and a communication interface, which are coupled together by a bus or other communication link, although other numbers and/or types of network devices could be used. The server devices in this example can host data associated with the additional sensors, or other patient data.

The client devices in this example include any type of computing device that can interface with the cardiac monitoring computing device to submit data and/or receive GUI(s). Each of the client devices in this example includes a processor, a memory, and a communication interface, which are coupled together by a bus or other communication link, although other numbers and/or types of network devices could be used.

The client devices can run interface applications, such as standard web browsers or standalone client applications, which may provide an interface to communicate with the cardiac monitoring computing device via the communication network(s). The client devices may further include a display device, such as a display screen or touchscreen, and/or an input device, such as a keyboard, for example. In one example, the client devices can be utilized by hospital staff to facilitate improved cardiac monitoring, although other types of client devices utilized by other types of users, such as the patient can also be used in other examples. In one example, the client devices receive data including patient information, such as name, date of birth, medical history, etc., for example. In other examples, this information is stored on one of the server devices.

Although the exemplary environment with the cardiac monitoring computing device, server devices, client devices, image sensor, additional sensors, and communication network(s) are described and illustrated herein, other types and/or numbers of systems, devices, components, and/or elements in other topologies can be used. It is to be understood that the systems of the examples described herein are for exemplary purposes, as many variations of the specific hardware and software used to implement the examples are possible, as will be appreciated by those skilled in the relevant art(s).

One or more of the devices depicted in the environment, such as the cardiac monitoring computing device, client devices, or server devices, for example, may be configured to operate as virtual instances on the same physical machine. In other words, one or more of the cardiac monitoring computing device, client devices, or server devices may operate on the same physical device rather than as separate devices communicating through communication network(s). Additionally, there may be more or fewer cardiac monitoring computing devices, client devices, or server devices than illustrated in FIG. 1.

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only wireless networks, cellular networks, PDNs, the Internet, intranets, and combinations thereof.

The examples may also be embodied as one or more non-transitory computer readable media (e.g., the memory) having instructions stored thereon for one or more aspects of the present technology as described and illustrated by way of the examples herein. The instructions in some examples include executable code that, when executed by one or more processors (e.g., the processor(s)), cause the processor(s) to carry out steps necessary to implement the methods of the examples of this technology that are described and illustrated herein.

An exemplary method of cardiac monitoring using fused sensor data, including both image data and non-image data, will now be described with reference to FIG. 3. First, the cardiac monitoring computing device receives image data from an image sensor configured for monitoring edema in a patient in block 301. By way of example, the image sensor may be the system for detecting edema as disclosed in U.S. Patent Application Publication No. 2019-0231260, the disclosure of which is hereby incorporated by reference in its entirety. For example, the image sensor can include a light source configured to irradiate a tissue of the patient with light. The tissue could be located in the patient's forearm, although other tissue locations could be utilized. The image sensor also includes a detector configured to collect reflected light from the tissue of the patient and generate the image data associated with the reflected light. The image data can be received and used to calculate intensity values to determine whether the tissue exhibits symptoms of edema as described in U.S. Patent Application Publication No. 2019-0231260, the disclosure of which is hereby incorporated by reference in its entirety. In one example, the image data can be processed on the cardiac monitoring computing device.

Next, in block 302 the cardiac monitoring computing device receives additional data from one or more additional sensors configured to monitor one or more factors related to cardiac activity of the patient. In one example, the data received from the additional sensors in non-image data relevant to the cardiac condition of the patient. The additional sensors can include can include a pulse oximeter (or other sensors configured to measure hemodynamics), an electrocardiogram (ECG or EKG), a sensor for measuring thoracic impedance, or an implantable cardiac monitoring device, although any other sensors capable of measuring data relevant to cardiac activity could be employed. In another example, the cardiac monitoring computing device can receive additional data from one or more of the server devices or client devices.

In block 303, the cardiac monitoring computing device fuses the received image data from the image sensor with the received additional data from the one or more additional sensors to generate a fused data set. The cardiac monitoring computing device utilizes applies one or more data fusion algorithms the received image data and the received additional data in order to generate the fused data set. By way of example, the cardiac monitoring computing device uses one or more of an image weighted Bayesian function, logistic regression, linear regression, regression with regularization, naïve Bayes, classification and regression tress, support vector machines, relevance vector machines, (RVM), least angle regression, linear discriminant analysis, or a neural network, although other data fusion techniques or systems may be employed.

Next, in block 304 the cardiac monitoring computing device determines a cardiac condition for the patient based on the fused data set. In one example, the cardiac monitoring computing device can apply one or more machine learning models to the fused data set to determine the cardiac condition. The cardiac monitoring computing device can store and/or obtain training data related to the cardiac condition determination based on fused data sets from image and non-image sensors. The cardiac monitoring computing device can generate or train a machine learning model based on the training data and the generated fused data set. In one example, the machine learning model is a neural network, such as an artificial or convolutional neural network, although other types of neural networks or machine learning models can also be used in other examples. In one example, the neural network is a fully convolutional neural network. The generated fused data set in the previous step can be evaluated using the trained model to determine the patient's cardiac condition.

Next, in one implementation depicted by block 305, the cardiac monitoring computing device identifies whether there is a potential failure. If no, the process is repeated from the beginning to collect additional data for monitoring the cardiac condition of the patent. The generated fused data set can then be used to further train the machine learning model. If a potential failure is identified, then an alert is output to one or more of the server devices and/or client devices. Although an example of provide information based on a potential failure is described, the determined cardiac condition can also be utilized to provide treatment regimen changes, or other information to the patient and/or health care provided.

With this technology, image data related to peripheral edema is fused with non-image sensor data relevant to cardiac monitoring to provide a practical application of a more efficient and effective method of monitoring cardiac activity. The technology advantageously combines the multiple sensor logics to provide earlier warning of potential cardiac failure, or other cardiac issues. The technology can further be used to provide improved tele-monitoring of patients with heart-related issues.

In certain embodiments of the disclosure, the cardiac monitoring computing device generates an objective measure of cardiac health in block 306. For example, the objective measure can be a relative probability of a cardiac condition. In other examples, the objective measure is a composite indicator that indicates the degree of severity of a patient's edema. By generating an objective, numerical measure of a patient's cardiac health, including the severity of the patients edema, clinicians can better anticipate or adjust the level and types of intervention that are given to the patient. Still further, the cardiac monitoring computing device can record the generated objective measures over time, which enables clinicians to even further predict the health of a particular patient.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A method of cardiac monitoring, the method comprising:
   receiving, by a cardiac monitoring computing device, image data from an image sensor configured for monitoring edema in a patient, wherein the image sensor comprises;
   a light source configured to irradiate a tissue of the patient with light; and
   a detector configured to collect reflected light from the tissue of the patient and generate the image data associated with the reflected light;
   receiving, by the cardiac monitoring computing device, the image data associated with the reflected light;
   calculating, by the cardiac monitoring computing device, intensity values for reflected light;
   determining, by the cardiac monitoring computing device, whether the tissue exhibits symptoms of edema;
   receiving, by the cardiac monitoring computing device, additional data from one or more additional sensors configured to monitor one or more factors related to cardiac activity of the patient;
   fusing, by the cardiac monitoring computing device, the received image data with the received additional data from the one or more additional sensors to generate a fused data set; and
   determining, by the cardiac monitoring computing device, a cardiac condition for the patient based on the fused data set.

2. The method of claim 1, wherein fusing the received image date with the received additional data further comprises:
   applying, by the cardiac monitoring computing device, one or more data fusion algorithms to the received image data and the received additional data.

3. The method of claim 2, wherein applying the data fusion algorithm comprises utilizing one or more of an image weighted Bayesian function, logistic regression, linear regression, regression with regularization, naïve Bayes, classification and regression tress, support vector machines, or a neural network.

4. The method of claim 1, wherein the received additional data is non-image data.

5. The method of claim 1, wherein the one or more additional sensors comprise one or more of a pulse oximeter, an electrocardiogram machine, a sensor for thoracic impedance, or an implantable cardiac monitoring device.

6. The method of claim 1, wherein the determining the cardiac condition further comprises:
   identifying, by the cardiac monitoring computing device, one or more indications of a potential heart failure.

7. The method of claim 1, wherein the tissue of the patient is located on a forearm of the patient.

8. The method of claim 1, wherein the image data is spectral data and the image sensor is a spectral sensor.

9. A non-transitory computer readable medium having stored thereon instructions for improved cardiac monitoring comprising executable code that, when executed by one or more processors, causes the one or more processors to:
   receive image data from an image sensor configured for monitoring edema in a patient, wherein the image sensor comprises;
   a light source configured to irradiate a tissue of the patient with light; and
   a detector configured to collect reflected light from the tissue of the patient and generate the image data associated with the reflected light;
   receive the image data associated with the reflected light;
   calculate intensity values for reflected light;
   determine whether the tissue exhibits symptoms of edema;
   receive additional data from one or more additional sensors configured to monitor one or more factors related to cardiac activity of the patient;
   fuse the received image data with the received additional data from the one or more additional sensors to generate a fused data set; and
   determine a cardiac condition for the patient based on the fused data set.

10. The non-transitory computer readable medium of claim 9, wherein the processors fuse the received image data with the received additional data by applying one or more data fusion algorithms to the received image data and the received additional data.

11. The non-transitory computer readable medium of claim 10, wherein the data fusion algorithm includes one or more of an image weighted Bayesian function, logistic regression, linear regression, regression with regularization, naïve Bayes, classification and regression tress, support vector machines, or a neural network.

12. The non-transitory computer-readable medium of claim 9, wherein the additional data that the processors receive is non-image data.

13. The non-transitory computer readable medium of claim 9, wherein the one or more additional sensors comprise one or more of a pulse oximeter, an electrocardiogram machine, a sensor for thoracic impedance, or an implantable cardiac monitoring device.

14. The non-transitory computer-readable medium of claim 9, wherein determination of the
   cardiac condition further comprises:
      identifying one or more indications of a potential heart failure.

15. A cardiac monitoring computing device comprising memory comprising programmed instructions stored thereon for cardiac monitoring and one or more processors coupled to the memory and configured to execute the stored programmed instructions, which when the programmed instructions are executed the cardiac monitoring computing device:
- receives image data from an image sensor configured for monitoring edema in a patient, wherein the image sensor comprises;
  - a light source configured to irradiate a tissue of the patient with light; and
  - a detector configured to collect reflected light from the tissue of the patient and generate the image data associated with the reflected light;
- receives the image data associated with the reflected light;
- calculates intensity values for reflected light;
- determines whether the tissue exhibits symptoms of edema;
- receives additional data from one or more additional sensors configured to monitor one or more factors related to cardiac activity of the patient;
- fuses the received image data with the received additional data from the one or more additional sensors to generate a fused data set; and
- determines a cardiac condition for the patient based on the fused data set.

16. The cardiac monitoring computing device of claim 15, wherein the processors fuse the received image data with the received additional data by applying one or more data fusion algorithms to the received image data and the received additional data.

17. The cardiac monitoring computing device of claim 16, wherein the data fusion algorithm includes one or more of an image weighted Bayesian function, logistic regression, linear regression, regression with regularization, naïve Bayes, classification and regression tress, support vector machines, or a neural network.

18. The cardiac monitoring computing device of claim 15, wherein the additional data that the processors receive is non-image data.

19. The cardiac monitoring computing device of claim 15, wherein the one or more additional sensors comprise one or more of a pulse oximeter, an electrocardiogram machine, a sensor for thoracic impedance, or an implantable cardiac monitoring device.

20. The cardiac monitoring computing device of claim 15, wherein determining the cardiac condition further comprises:
- identifying one or more indications of a potential heart failure.

21. The cardiac monitoring computing device of claim 15, wherein the image data is spectral data and the image sensor is a spectral sensor.

* * * * *